United States Patent [19]
Prentiss

[11] Patent Number: 5,690,679
[45] Date of Patent: *Nov. 25, 1997

[54] INFANT FEEDING CONTAINER

[76] Inventor: John Gilbert Prentiss, P.O. Box 15458, Santa Fe, N. Mex. 87506-5458

[*] Notice: The portion of the term of this patent subsequent to Sep. 30, 2009, has been disclaimed.

[21] Appl. No.: 814,565

[22] Filed: Dec. 30, 1991

[51] Int. Cl.$^6$ .................................................. A61J 17/00
[52] U.S. Cl. ................................ 606/236; 215/11.6
[58] Field of Search .................................. 128/848, 859; 606/234, 235, 236; 215/11.6, 100

[56] References Cited

U.S. PATENT DOCUMENTS

| | | | |
|---|---|---|---|
| 1,429,198 | 9/1922 | Fawcett | 215/11.6 |
| 1,438,272 | 12/1922 | Snyder | 215/11.6 |
| 1,462,291 | 7/1923 | McCrink | 215/11.6 |
| 1,518,823 | 12/1924 | Schmidt | 606/236 |
| 3,650,271 | 3/1972 | Pelli | 128/252 |
| 4,481,949 | 11/1984 | Kesslring | 606/236 |
| 4,526,274 | 7/1985 | Kesselring | 215/11.6 |
| 4,586,621 | 5/1986 | Dahan | 215/11 |
| 5,129,532 | 7/1992 | Martin | 606/236 |

*Primary Examiner*—Michael A. Brown

[57] ABSTRACT

The present infant feeding container attempts to simulate as much as possible the sensation of a mother's breast, avoiding many of the drawbacks attendant with conventional artificial means of breast feeding. The container is ideally breast-shaped and fabricated of a resilient material resembling a natural breast. Having a wider base than elongate cylindrical bottles of equal volume, a more stable container is provided. Included is a rack suitable for holding the container for content heating and sterilization. The improved sensory experience facilitated by these innovations is expected to far more closely approximate the experience of natural breast feeding and some of the benefits attendant thereto.

4 Claims, 3 Drawing Sheets

INFANT FEEDING CONTAINER

BACKGROUND

1. Field of Invention

The present invention relates to infant feeding containers, more specifically one which is approximately in the form of a breast.

2. Prior Art

The natural way of feeding infants is by breast feeding. Breast feeding is preferred by many for reasons including the importance of bonding the mother and infant, as well as the superior quality of natural mother's milk. However, breast feeding is not always possible for mothers unable to lactate sufficiently for the mother to provide for the baby's needs. Mothers who are engaged in full-time employment or are otherwise unable or unwilling to nurse their babies require an artificial container from which their babies can suckle. With recent changes in society in industialized countries, increasingly more fathers are raising infants, using one of several bottle feeders now widely available. Current feeding means include the conventional elongate cylindrical bottle of glass or plastic, equipped with a cap and latex nipple. More recent containers have a similar shape but are equipped with collapsable liners that enable the infant to consume the contents without ingesting as much air in the stomach.

Several disadvantages exist with the current artificial means of feeding infants, the greatest no doubt being the unnaturalness of ingesting milk from a cylindrical bottle of hard and angular material. A second disadvantage is the fact that a conventional cylindrical bottle has a relatively small base and is very easily tipped over by an infant. Glass and plastic bottles may even be broken at times. A tipped over bottle often leads to contamination of the nipple as well, a problem that is seldom properly remedied once the feeding process has begun.

Another problem with baby bottles of the rigid cylinder type is that they are typically difficult to fully clean, since the bottle bottom can only be reached with a bottle brush to remove any dried on residues.

Glass and plastic cylindrical bottles are hard for infants to hold and may be quite hot as well. Other disadvantages include the depth of water required to fully immerse a long, cylindrical bottle when heating.

Disclosure of the Invention

The present invention is the construction of an infant feeding container in the approximate shape of a breast. Furthermore, an infant feeding container predominantly of a resilient material such as latex, neoprene or other rubber-like material is envisioned to simulate far more directly the experience of natural breast feeding.

Objects and advantages of the present invention include, in addition, far better container stability and ease of handling by the user infant. In breast-like designs having removable bases, ease of cleaning is greatly facilitated so that a brush need not be used. Furthermore, a shallow pan may be effectively used to heat and to sterilize the entire container in water.

The use of resilient material in the construction of the predominance of the container makes the vessal essentially unbreakable as well as providing the infant with a somewhat soft and cuddly container to hold, thereby much enhancing the infant's sensory experience to more closely approximate direct human contact. Additional benefit is derived from the fact that the collapsable container walls are less apt to cause an infant to ingest air into the stomach while feeding.

While many alternatives obviously exist for the construction of the present invention, such as removable nipples, various nuances of shape and types of closure for the bottom when used as a filling/cleaning point, it is intended that the appended drawings depict the spirit of the present invention only, incorporated in demonstrative preferred embodiments. The claims more fully delineate the art intended to be protected hereby, and the drawings should in no way serve to limit said claims. The territory is as diverse in nuance of size, shape and color as are women's breasts.

DETAILED DESCRIPTION OF THE DRAWINGS

Figure 1:
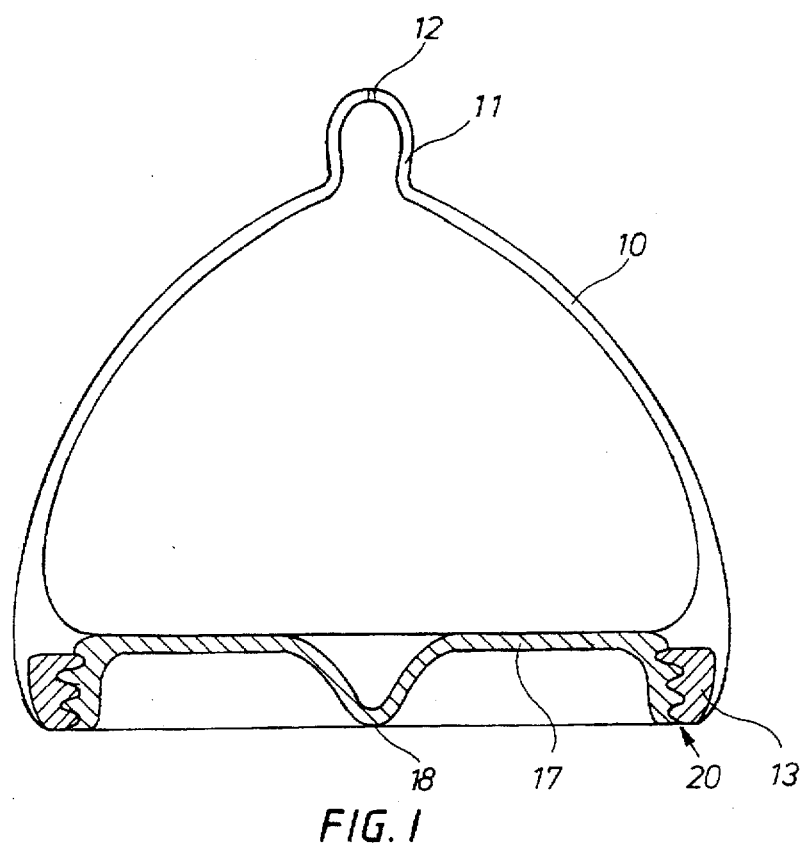
FIG. 1 is a cross section of a breast shaped infant feeding container having an integral nipple and removable base.
Figure 2:
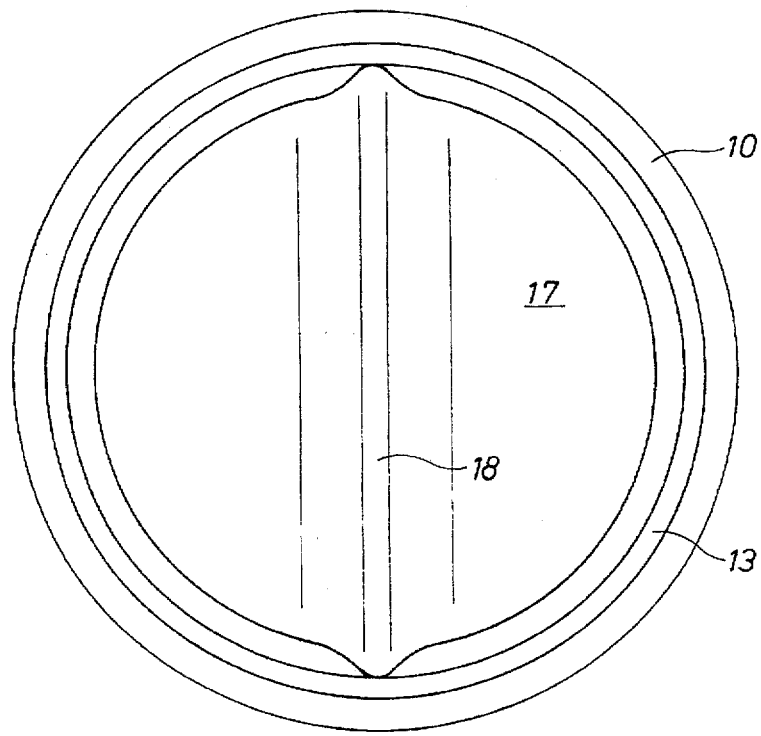
FIG. 2 is a bottom view of FIG. 1.

Referring now to FIG. 1 of the drawings, the container walls 10 are formed in the approximate shape of a breast, with an integral nipple 11 having ducts 12. The container walls 10 are affixed to a threaded annular member 13 into which a threaded lid 17 is screwed. A grip 18 is provided, as shown in plan view in FIG. 2. Referring again to FIGS. 1 and 2, the container walls 10 may be ideally made of a rubber-like material to simulate a human breast. The walls 10 are bonded to the annular member 13, constructed of any non-toxic, anticorrosive material such as a high temperature plastic. The lid 17 is formed of a similar material to create a watertight seal. The annular member 13 and lid 17 together must provide adequate strength so that the container will withstand considerable impact without leakage, It will be further noted that the composite parts of the base 20 form a gripping means suitable for an infant's fingertips. Ideally, all the surfaces of the container should be smooth and sculpted, yet easy to grasp.

Figure 3:
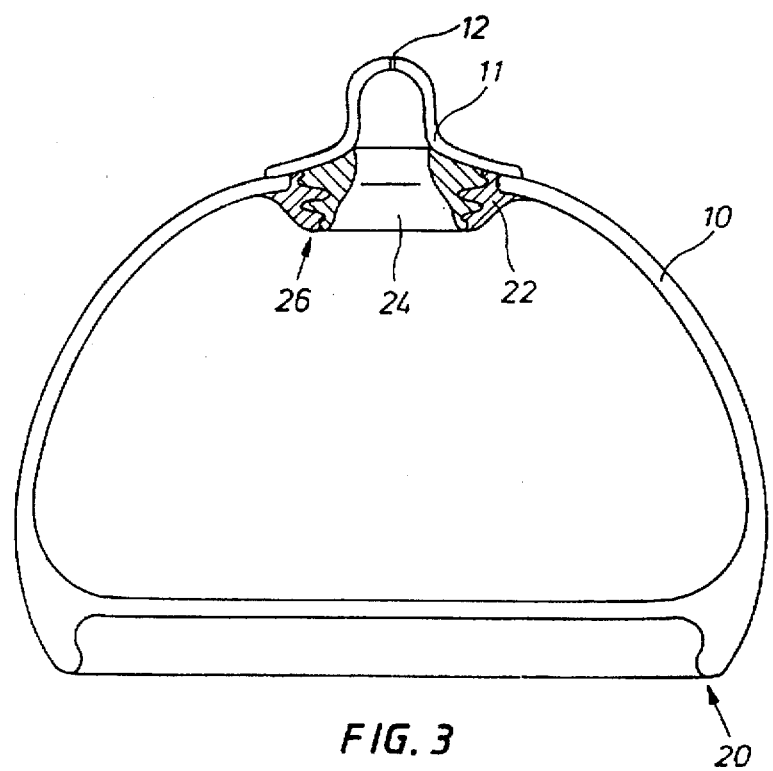
FIG. 3 is a cross section of a breast-shaped infant feeding container having an integral base and removable nipple.

Referring now to FIG. 3, the container walls 10, and the base 20 form an intergal containment vessal, to which is attached a threaded top annular member 24. A nipple 11 with ducts 12 is secured to a second threaded annular member 22 which screws into said annular member 24 to provide a watertight seal. The nipple 11 is flanged to cover the rigid annular members 22 and 24 so as to provide a soft, breast-like surface for contact with the infant's face. When constructed of a pliable material, cleaning of this vessal is relatively easy without resorting to a bottle brush. The nipple assembly 26 may be provided with several radial holes in the flange into which a cap with pins corresponding to said holes may be employed to screw and unscrew the nipple as well as to protect it when not in use.

Figure 4:
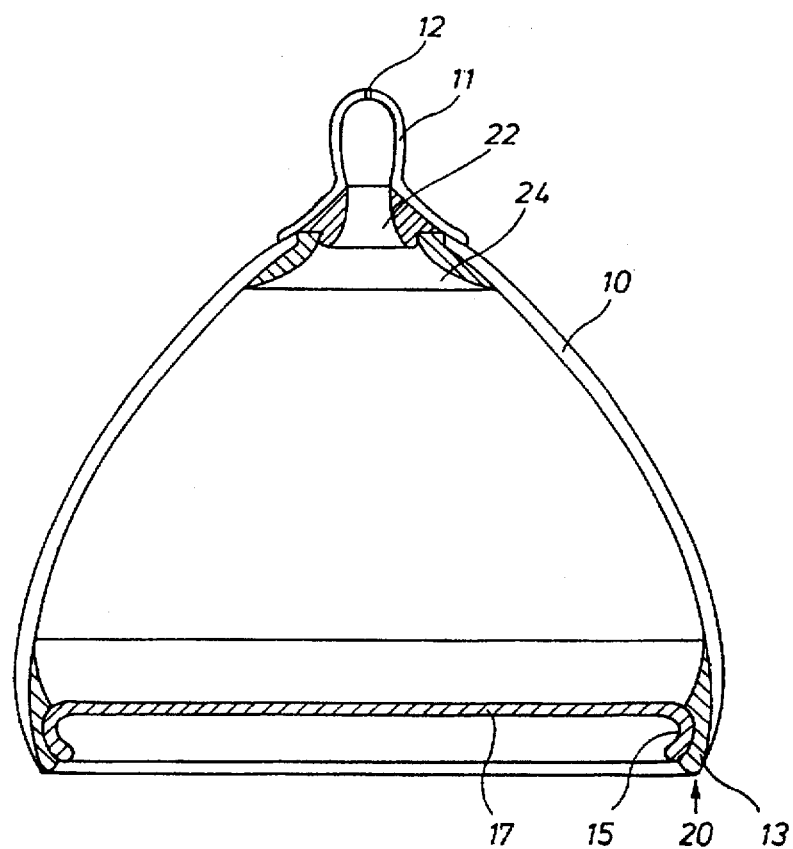
FIG. 4 is a cross section of a breast-shaped infant feeding container having a snap-in, replaceable nipple and a comparable snap-in base.

FIG. 4 depicts another sample variation of the ways in which the subject invention may be embodied. Container walls 10 are bonded to top and bottom annular members, 24 and 13 respectively, said annular members having a cam-shaped cross section into which corresponding top and bottom annular members 22 and 15 respectively secruely fasten to form a water tight seal. The nipple 11 and the lid 17 may be integral with the annular members, 22 and 15, or, particularly in the case of the nipple 11, may be made of a more pliable material and bonded to more rigid annular members.

Figure 5:
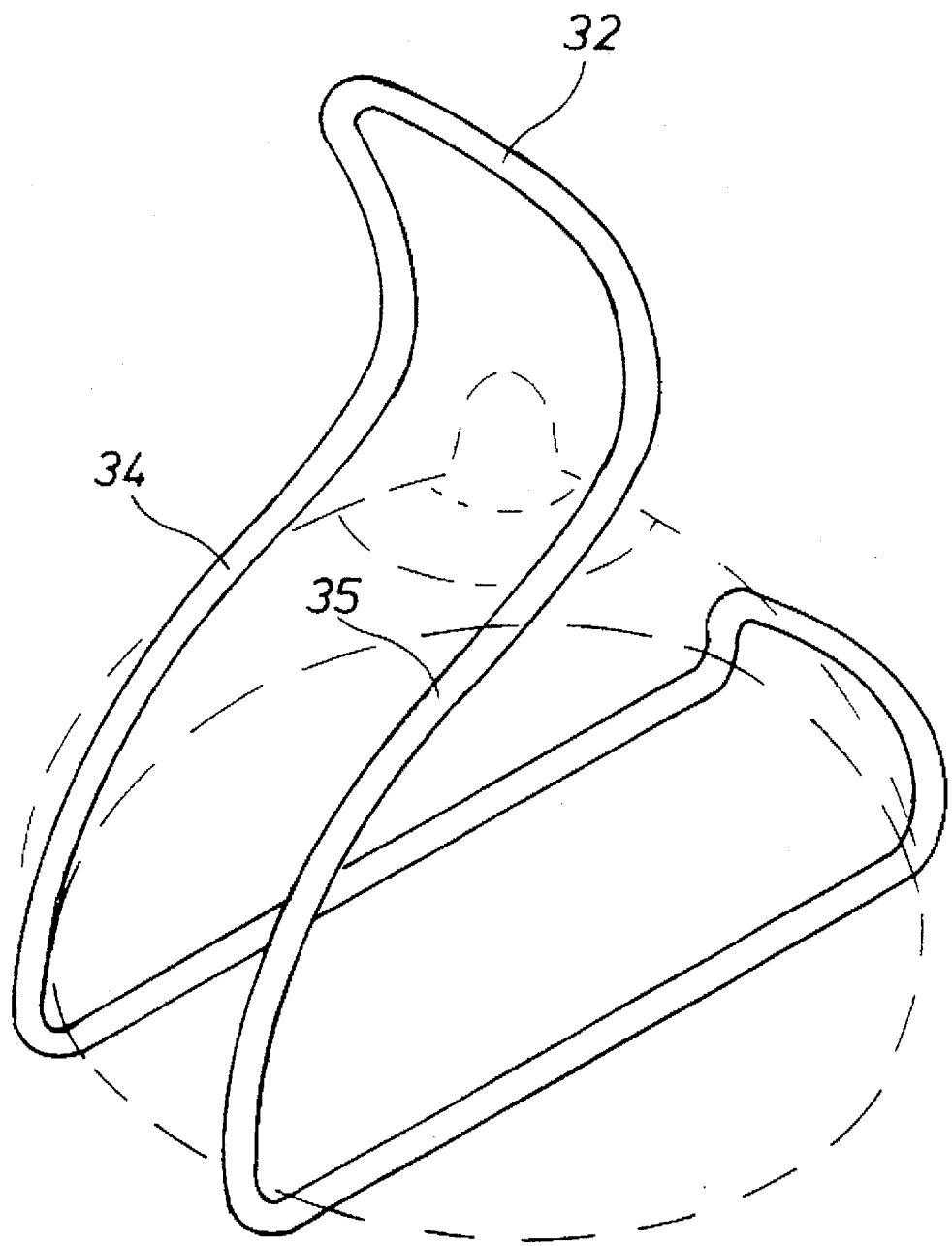
FIG. 5 is a perspective of a rack used to lift the subject invention for the purpose of heating the contents or sterilization of the container.

Referring now to FIG. 5, a wire rack is depicted in perspective with a typical breast-shaped container (in dotted lines) resting in the cradle provided. A handle 32 is likewise provided for lifting the assembly in and out of boiling water or other heat source for sterilization and warming of the container contents. The breast-shaped container is retained between uprights 34 and 35, yet is easily removed from the rack,

I claim:

1. An infant feeding container wherein the feeding experience will closely resemble that of natural breast feeding, said container comprising a dome shaped member approximately in the form of a human female breast and a base, said dome shaped member having a crest, resilient walls, and a ducted nipple centrally disposed at said crest of said dome shaped member through which an infant may withdraw liquid nourishment, said base including a graspable annular member which is more rigid than said resilient walls and shaped to form a gripping means suitable for an infant's fingertips, said base further including means, attached to said graspable annular member, for closing said dome shaped member to provide a closed interior space for holding liquids.

2. The infant feeding container of claim 1, wherein said means for closing said dome shaped member is a detachable lid.

3. The infant feeding container of claim 1, wherein said means for closing said dome shaped member is formed integral with said graspable annular member.

4. The infant feeding container of claim 3, wherein said ducted nipple is detachable from said dome shaped member.

* * * * *

UNITED STATES PATENT AND TRADEMARK OFFICE
CERTIFICATE OF CORRECTION

PATENT NO. : 5,690,679

DATED : Nov. 25, 1997

INVENTOR(S) : John Gilbert Prentiss

It is certified that error appears in the above-identified patent and that said Letters Patent is hereby corrected as shown below:

Title page, item [*]    Notice should read --The terminal 27 months of this patent has been disclaimed.--

Signed and Sealed this

Twelfth Day of May, 1998

Attest:

BRUCE LEHMAN

Attesting Officer    Commissioner of Patents and Trademarks